United States Patent [19]

Bischofberger

[11] Patent Number: 5,733,788
[45] Date of Patent: Mar. 31, 1998

[54] PMPA PREPARATION

[75] Inventor: Norbert W. Bischofberger, San Carlos, Calif.

[73] Assignee: Gilead Sciences, Inc., Foster City, Calif.

[21] Appl. No.: 686,829

[22] Filed: Jul. 26, 1996

[51] Int. Cl.⁶ ................................................ G01N 30/02
[52] U.S. Cl. ........................... 436/98; 436/161; 544/244
[58] Field of Search ......................... 436/98, 161

[56] References Cited

U.S. PATENT DOCUMENTS 4,808,716  2/1989  Holy et al. .......................... 544/244

FOREIGN PATENT DOCUMENTS

WO 94/03467  2/1994  WIPO.

OTHER PUBLICATIONS

Tsai et al., "Prevention of SIV Infection in Macaques by (R)-9-(2-Phosphonylmethoxypropyl)adenine," Science 270:1197–1199 (Nov. 17, 1995).

*Primary Examiner*—Robert T. Bond
*Attorney, Agent, or Firm*—Max D. Hensley

[57] ABSTRACT

Purified preparations of PMPA are provided, together with analytical methods for the detection of undesired contaminants in PMPA preparations. The PMPA compositions of the invention are of particular utility in therapeutics intended for the treatment or prophylaxis of viral infections.

3 Claims, 1 Drawing Sheet

PMPA PREPARATION

BACKGROUND OF THE INVENTION

This invention is concerned with compositions containing (R)-9-[2-phosphonomethoxy)propyl]adenine or intermediates therefor.

PMPA is a highly potent antiviral agent having particular potential for the therapy or prophylaxis of retroviral infections. The racemate is disclosed in U.S. Pat. No. 4,808,716 and the chirally pure (R) enantiomer is described in WO 94/03467. The antiviral specificity of PMPA is well known, as is its use for antiviral therapy and propylaxis. See for example Tsai et al., Science 270:1197-1199 (1995).

PMPA intended for use in therapeutic applications should be highly purified. This invention is concerned with the removal of undesired contaminants from PMPA preparations.

SUMMARY OF THE INVENTION

In accordance with this invention a PMPA composition is provided that is greater than about 95% PMPA by weight and that contains less than about 0.02% by weight of a contaminant having an HPLC retention time relative to PMPA of 0.38, 0.64, 1.2, 1.4, 1.49, 1.51, 1.6, 1.8, or 1.9.

In another embodiment of the invention, a PMPA composition is provided that is greater than about 95% PMPA by weight and that contains less than about 0.02% by weight of at least one contaminant found in trace 1 of FIG. 1 which is not found in trace 2 of FIG. 1.

In a further embodiment of the invention, a PMPA composition is provided that is greater than about 95% PMPA by weight and that contains less than about 0.02% by weight of a contaminant selected from the group consisting of bisPMPA adduct, adenine, hydroxypropyl adenine or propenyl adenine.

Another embodiment of this invention comprises analyzing a PMPA composition to determine the presence or absence of at least one contaminant having an HPLC retention time relative to PMPA of 0.38, 0.64, 1.2, 1.4, 1.49, 1.51, 1.6, 1.8 or 1.9.

Another embodiment of this invention comprises analyzing a PMPA composition to determine the presence or absence of at least one contaminant found in trace 1 of FIG. 1 which is not found in trace 2 of FIG. 1.

Another embodiment of this invention comprises analyzing a PMPA composition to determine the presence or absence of at least one contaminant selected from the group of bisPMPA adduct, hydroxypropyl adenine and propenyl adenine.

A further embodiment of this invention comprises purifying a PMPA composition to reduce the concentration in the composition of a contaminant having an HPLC retention time relative to PMPA of 0.38, 0.64, 1.2, 1.4, 1.49, 1.51, 1.6, 1.8 or 1.9.

A further embodiment of this invention comprises purifying a PMPA composition to reduce the concentration in the composition of a contaminant found in trace 1 of FIG. 1 which is not found in trace 2 of FIG. 1.

A further embodiment of this invention comprises purifying a PMPA composition to reduce the concentration in the composition of a contaminant selected from the group of bisPMPA adduct, hydroxypropyl adenine and propenyl adenine.

A further embodiment of this invention comprises purifying a PMPA composition containing greater than about 95% by weight PMPA to reduce the concentration in the composition of a contaminant selected from the group of bisPMPA adduct, adenine, hydroxypropyl adenine and propenyl adenine.

These and other embodiments of the invention will be apparent to the artisan upon consideration of this specification as a whole.

DETAILED DESCRIPTION OF THE INVENTION

Figure 1:
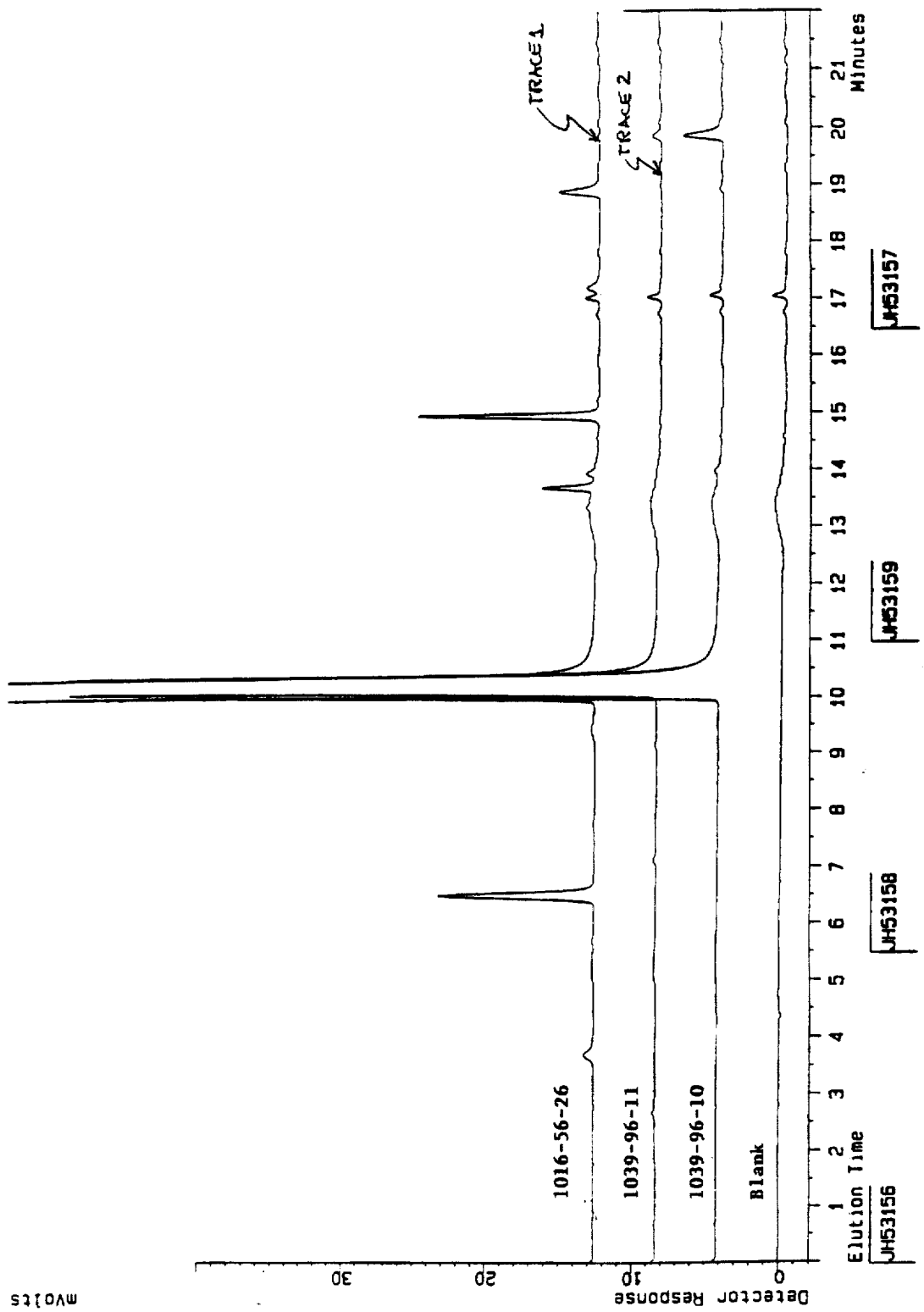
FIG. 1 is a superimposed HPLC trace of three lots of PMPA. Lot 1016-56-26 contains peaks representing contaminants not found in lot 1039-96-11, the trace immediately below that of lot 1016-56-26. The large peak at approximately 10 min. is PMPA. The compounds found under the non-PMPA peaks in contaminated lot 1016-56-26 are the focus of this invention.

PMPA means (R)-9-[2-(phosphonomethoxy)propyl] adenine and its protected intermediates. Protected intermediates include PMPA esters, e.g., alkyl esters, and PMPA analogues containing adenine $N^6$ protecting groups. Protected intermediates also means PMPA phosphonesters, phosphonoamidates and other adducts with groups that are removed by hydrolytic action or other cleavage processes in vivo, exemplary groups being found in WO 94/10539.

The identity of the PMPA compound is not critical since the contaminant targeted for removal can be separated during the synthesis of PMPA per se, in which case the contaminant is removed from a preparation of a PMPA intermediate, or it can be removed after PMPA has been converted into a prodrug that is not intended to be hydrolyzed until it is administered to a patient. In either case, the contaminant is not removed from PMPA per se but is removed from its protected intermediate. Typically, however, the contaminant will be removed from PMPA at an end stage of the PMPA synthesis method, i.e., when the concentration of PMPA has been raised to greater than about 95% by weight of the composition as a whole.

The contaminants that have been identified in a PMPA lot are identified by their retention relative to PMPA itself, or comparative analysis of peaks found in HPLC traces in contaminated PMPA lots as opposed to those devoid of the contaminants. The component contaminants in several suspect peaks have been characterized. They are a bis-adduct of PMPA (PMPA alkylated at a nitrogen by a methylenephosphonate group) at RRT 0.64, adenine at RRT 0.84, 9-(2-hydroxypropyl) adenine at RRT 1.4, and E/Z isomeric mixture of 9-(1-propenyl) adenine at RRT 1.9. The structural characterization of the remaining contaminants would be routine given the direction herein. Structural elucidation of the uncharacterized contaminants is readily accomplished, for example, by conventional methods of analytical chemistry, including NMR, mass spectroscopy, mass spectroscopy coupled with a chromatographic separation and the like.

In general, the undesired contaminant should be present at a concentration less than about 0.02% by weight of a composition containing greater than about 95% by weight PMPA, ordinarily less than about 0.01% and usually less than about 0.005%. In some embodiments, the composition may be entirely free of contaminant. In compositions containing less than about 95% by weight of PMPA, the concentration of contaminant usually will less than about 0.019%, ordinarily less than about 0.0095%, and usually less than about 0.00475% by weight of the PMPA in the composition. The quantities of contaminant are approximate and will be understood to vary somewhat with the analytical method employed.

Of the structurally elucidated contaminants, propenyl adenine, hydroxypropyl adenine and the PMPA adduct are the preferred contaminants for removal. In accordance with this invention any one or combination of the three contaminants are removed as set forth herein. With respect to the contaminants as characterized by relative retention time, those with RRTs of 0.64, 1.4, 1.6 and 1.9 are preferred for removal. However, any one or combination of contaminants with RRTs of 0.38, 0.64, 1.2, 1.4, 1.49, 1.51, 1.6, 1.8 or 1.9 are removed or reduced in accordance with this invention, for example by recrystallization or chromatographic separation (HPLC, anion or cation exchange columns) immunoaffinity purification and other physico-chemical separation method.

All citations are expressly incorporated herein by reference.

The following examples are illustrative and are not to be construed as limiting the invention.

EXAMPLES

Example 1

2. Synthesis Description
   Process Summary (S)-Glycidol is reduced to (R)-1,2propanediol by catalytic hydrogenation and is then reacted with diethyl carbonate to afford (R)-1,2-propylene carbonate. The carbonate is treated with adenine and catalytic sodium hydroxide to give (R)-9-[2-(diethylphosphonomethoxy)propyl]adenine which, without isolation, is reacted with lithium hydride and diethyl p-toluenesulfonyl-oxymethylphosphonate (prepared by reacting diethyl phosphite and paraformaldehyde, and tosylating the product in situ). The resulting (R)-9-[2-diethylphosphonomethoxypropyl]adenine is deesterified with bromotrimethylsilane to give crude PMPA, which is then purified by crystallization from water with pH adjustment. The dried, purified product is hydrated by slurrying with water and acetone to afford PMPA monohydrate.

Step 1. (R)-1,2-Propanediol: (S)-Glycidol (997 g, 13.6 moles) (note that the scale of this method is proportionately reduced if desired) is added to a suspension of ammonium formate (908 g, 14.4 moles) and 10% palladium on carbon (170 g) in denatured ethanol (11 kg) and stirred at approximately 22° C. for 24 hours until the glycidol is consumed as determined by TLC. The solids are removed by filtration and the flitrate is concentrated in vacuo at no more than 50° C. After adding sodium methoxide in methanol, 25% w/w (1 molar equivalent relative to formate content of diol, estimated by $^1$H NMR) to the residual oil, fractional vacuum distillation of the mixture at 105° to 130° C., 20–40 mm Hg PMPA Process Flow Diagram

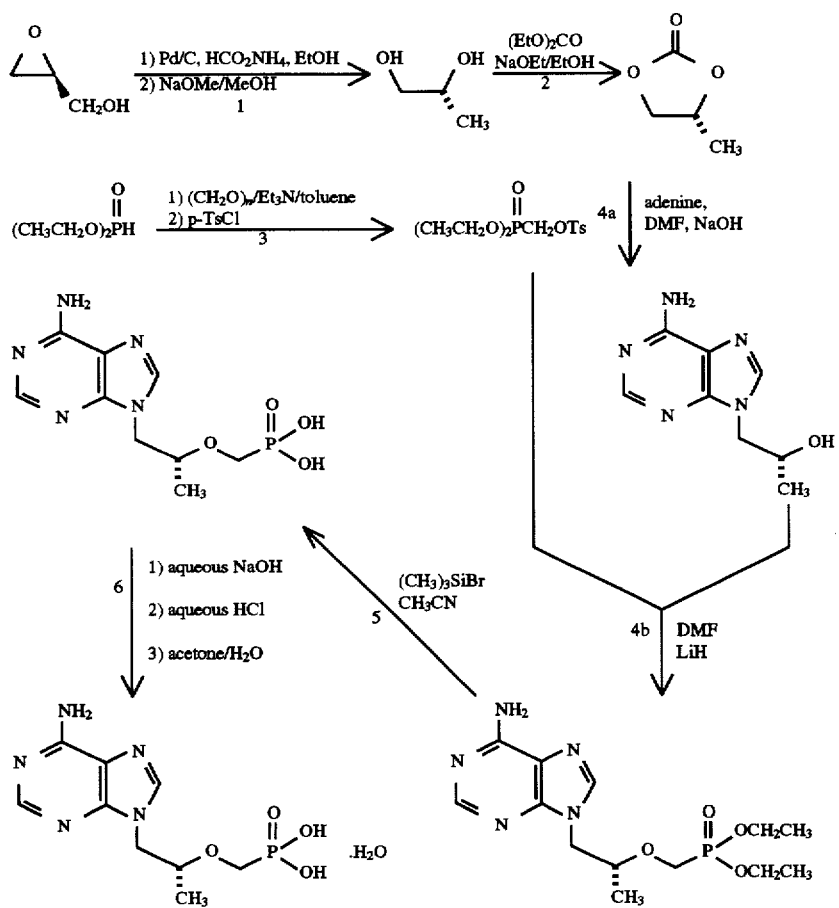

affords a 76% (779 g) yield of the title compound. The product purity is typically greater than 90% (estimated by $^1$H NMR analysis).

Step 2. (R)-1,2-Propylene carbonate: A mixture of diethyl carbonate (6.56 kg, 55.5 moles), sodium ethoxide in ethanol (21% w/w, 0.82 kg, 2.5 moles) and (R)-1,2-propanediol (3.84 kg, 50.5 moles) is heated at 80° to 150° C., while the ethanol is allowed to distill out of the pot. Additional diethyl carbonate may be added, followed by distillation of ethanol, if the reaction does not reach completion. When all propanediol is consumed as shown by TLC, the mixture is distilled at 120° C., 10–17 mm Hg, to furnish a 92% (4.75 kg) yield of the title compound as a colorless liquid. The product purity is typically 96% or greater by GC analysis.

Step 3. Diethyl p-toluenesulfonyloxymethylphosphonate: A mixture of diethyl phosphite (280 kg, 2,030 moles), paraformaldehyde (77 kg, 2,560 moles), and triethylamine (21 kg, 210 moles) in toluene (980 kg) is heated at 84° to 110° C. for 2 hours, then under reflux for 1 hour, until no diethyl phosphite is detectable by TLC. The solution is cooled to below 10° C. and p-toluenesulfonyl chloride (350 kg, 1,840 moles) and triethylamine (288 kg, 2,850 moles) are added while the temperature is kept at no more than 10° C. The resulting mixture is warmed to 22° C. and stirred for approximately 5 hours, until TLC indicates the p-toluenesulfonyl chloride consumed. The solids are removed by filtration and washed with toluene (approximately 350 kg). The combined washings and filtrate are washed either twice with water (approximately 400 kg each), or optionally with a sequence of water, 5% aqueous sodium carbonate, and twice with water. In the event emulsion occurs, brine may be added to the first organic/water mixture. The organic phase is distilled in vacuo at no more than 50° C. to LOD no more than 10% and water content, by KF titration, no more than 0.5%, affording 60–70% (350–420 kg) yield of the title compound as an oil of about 85–95% purity, exclusive of toluene.

Step 4. (R)-9-[2-(Diethylphosphonomethoxy)propyl]adenine: A mixture of adenine (5.2 kg, 38.3 moles), sodium hydroxide (61.2 g, 1.5 moles), (R)-1,2-propylene carbonate (4.3 kg, 42.1 moles), and N,N-dimethylformamide (36 kg) is heated at 132° to 138° C. for 18–36 hours until only a trace of adenine remains as shown by area normalized HPLC. The resulting mixture is cooled to 80° to 100° C. and concentrated in vacuo to remove approximately half of the solvent, producing the stage I intermediate. After cooling the residue to approximately 22° C., N,N-dimethylformamide (55 kg) and lithium hydride 95% dispersion in mineral oil (320 g, 38.2 moles) are added, and the mixture is stirred at 45° to 55° C. for 1–2 hours. Diethyl p toluenesulfonyloxymethylphosphonate (10 kg, 28.9 moles) is added and the mixture is stirred at 45° to 85° C. for 1–3 hours. After cooling to less than 50 ° C., more lithium hydride 95% dispersion in mineral oil (320 g, 38.2 moles) and then diethyl p-toluenesulfonyloxymethylphosphonate (10 kg, 28.9 moles) are added. The mixture is maintained at 45° to 85° C. until the reaction is complete in about 1–3 hours as shown by disappearance of the Stage I intermediate by area normalized HPLC. The mixture is cooled to approximately 22° C. and glacial acetic acid (2.0 kg, 33.3 moles) is added. The resulting mixture is filtered and the flitrate is concentrated in vacuo at a final maximum pot temperature of 90° to 100° C. The residue is cooled to approximately 22° C., and is continuously extracted with dichloromethane (approximately 160 kg) for 12–48 hours. The combined, dichloromethane extracts are concentrated at no more than 90° C. giving a 50% (15.7 kg) yield of the title compound as a viscous, orange oil suitable for use in the following step. The product purity is typically 40–45%, measured by area normalized HPLC (approximately 20–30% assay by weight normalized HPLC).

Step 5. (R)-9-[2-(Phosphonomethoxy)propyl]adenine, crude: A mixture of crude (R)-9-[2-(diethylphosphonomethoxy)propyl]adenine (15.7 kg, approximately 11 moles), bromotrimethylsilane (20.0 kg, 131 moles), and acetonitrile (18.0 kg) is heated at reflux for 1–8 hours until deesterification is complete as shown by area normalized HPLC. The solvent is removed by distillation at no more than 100° C. and the residue is partitioned between water (22.0 kg) and ethyl acetate (19.8 kg) at 22° C. The isolated aqueous phase is adjusted to pH 3.1–3.3 with aqueous sodittm hydroxide. The resulting slurry is held at 0° to 10° C. for at least 3 hours. The solids are collected by filtration, washed sequentially with cold water (6.0 kg) and acetone (4.7 kg), and then dried in vacuo at no more than 80° C. to constant weight giving a 79% (2.54 kg) yield of the anhydrous, title compound.

Step 6. (R)-9-[2-(Phosphonomethoxy)propyl]adenine, pure: Aqueous sodium hydroxide (50%) is added to a suspension of crude (R)-9-[2-(phosphonomethoxy)propyl] adenine (2.4 kg) in sterile water for irrigation, USP or sterile water for injection, USP ("WFI") (11.5 kg) until pH 6.5–7.5 is obtained. The resulting solution is washed with ethyl acetate (10.4 kg), clarified by filtration, and acidified to pH 3.1–3.3 with hydrochloric acid causing precipitation of product. After stirring the slurry at 0° to 10° C. for at least 3 hours, the solids are collected by filtration, washed sequentially with cold WFI (approximately 3.5 kg) and acetone (approximately 2.5 kg), and then dried in vacuo at no more than 60° C. to constant weight. The dry solid is slurried with a mixture of acetone (17.2 kg) and WFI (2.8 kg) at 22° C. for at least 8 hours and then isolated by filtration, washed with a mixture of acetone (13 kg) and WFI (2 kg), and air dried to no more than 1% LOD, affording a 82% (1.9 kg) yield of the title compound as the monohydrate. The product purity is typically 98% or greater by both area normalized and weight normalized HPLC.

EXAMPLE 2

Multiple Recrystallization of PMPA To Remove Contaminants 0.75 g of PMPA from the title lot (preparation A) was recrystallized from H$_2$O (11.3 mL, 15:1 wt. ratio) by heating the suspension to 95°–100° C. Upon cooling to room temperature, the crystallized PMPA was chilled in a freezer. After 3 h the crystals were filtered on a coarse frit fit with TyvekTM™, the filter cake rinsed with ice-cold H$_2$O and acetone, and air dried to constant weight to give a fluffy white solid (Preparation B). Recovery was 0.64 g (85.3%). HPLC showed 98.5–98.9% pure PMPA. No 14.7 min impurity was observed. Recrystallized liquors (1039-91-23) showed 71.4% pure PMPA with a major impurity at 4.8 min (26.9%), possibly solvent. 14.7 min impurity=0.05%.

Preparation B PMPA was recrystallized again from 9.6 mL (15:1 wt. ratio) H$_2$O heated to 95°–100° C. Upon cooling to room temperature, the crystallized PMPA was chilled in a freezer overnight. The PMPA was filtered through a coarse frit fit with TyvekTM™ and the filter cake was rinsed with ice-cold H$_2$O and acetone, then sucked dry to constant weight to afford a fluffy, white solid (Preparation C). Recovery was 0.52 g (81.3%). HPLC (JH52807, JH52810) showed 99.3–99.5% pure PMPA. The largest impurity at 19 min.=0.22%. Recrystallized liquors showed 64.9% pure PMPA with 0.01% 14.7 min impurity and 0.09% 19 min impurity.

Preparation C PMPA (0.50 g) was recrystallized from approximately 7.5 mL boiling $H_2O$ (15:1 wt. ratio). Upon cooling to room temperature, the PMPA was filtered on a coarse frit fit with Tyvek™. The filter cake was rinsed with ice-cold $H_2O$ and acetone then sucked to dryness to afford a fluffy white solid (Preparation D). The filtrate was also concentrated to afford a white solid (Preparation E). Recovery: Filter cake: 0.41 g (82%), Filtrate: 0.08 g =0.49 g combined (98%). HPLC analysis showed the filtrate (Preparation E) was 99.9% pure.

EXAMPLE 3
HPLC Analysis

Lots 1016-056-26 and 1039-96-11, as well as lot 1278-A-1 and reference standard lot 964-187-31, were analyzed by HPLC under the following chromatographic conditions.

Mobile Phase A: 50 mM potassittrn phosphate buffer, pH 6.0. Weigh and transfer 11.94 grams of potassium phosphate, monobasic and 2.14 grams of potassium phosphate, dibasic into a 2 L volumetric flask. Add about 1800 mL of water (3.4) and stir or sonicate until dissolution is complete. Measure the pH and adjust to 6.0±0.1 with phosphoric acid or potassium hydroxide, if necessary. Dilute to volume with water. Filter through a 0.45 μm Nylon 66 filter.

Mobile Phase B: 50 mM potassium phosphate, pH 6.0: acetonitrile (70:30). Combine 350 mL of Mobile Phase A with 150 mL of acetonitrile.

Operating Parameters

Mobile Phase Gradient: Start at 100% mobile phase A with a 10 minute linear gradient to 15% mobile phase B, followed by a 10 minute linear gradient to 100% mobile phase B. Hold at 100% mobile phase B for 2 minutes.
Run Time: 22 minutes
Equilibration Delay: 10 minutes
Flow rate: 1.5 mL/min
Temperature: Ambient
Detection: UV at 260 nm
Injection volume: 10 μL

EXAMPLE 4
Standard and Sample Solution Preparation

Standard Solution: Accurately weigh approximately 35 mg of PMPA reference standard into a 100 mL volumetric flask. Add approximately 75 mL of mobile phase A to the flask and sonicate for 5 min or until the PMPA dissolves. Allow the flask to cool to room temperature, dilute to volume with mobile phase A and mix thoroughly by repeatedly inverting and shaking the solution in the volumetric flask. Prepare duplicate standard solutions (R1 and R2) for purity determination. For identity determination only, one standard solution may be used. The final concentration of the solutions is about 0.35 mg/mL. Applying the purity correction factor (CF) of the PMPA reference standard, calculate the corrected concentration for each of the standard solutions as follows. (Note: To ensure solution homogeneity, the standard and sample solutions must be thoroughly mixed with adequate inversion and shaking of the volumetric flasks).

Under the above chromatographic conditions, the retention time of the PMPA peak is typically in the range of 8 to 11 minutes.

$$\text{Corrected standard solution concentration (mg/mL)} = \frac{\text{reference standard weight (mg)}}{\text{standard solution dilution volume(mL)}} \times CF$$

where CF is the purity correction factor assigned to the PMPA reference standard, on the anhydrous basis.

Sample Solution: Prepare the same manner as the standard solution using the PMPA sample. Prepare duplicate sample solutions (S1 and S2) for purity determination. For identity or impurity content determination only, one sample solution may be used.

Using the following formula, calculate the corrected sample solution concentration by correcting the weight of the PMPA sample for water content, as determined by Karl Fischer titration.

$$\text{Corrected sample solution concentration (mg/mL)} = \frac{\text{sample weight (mg)}}{\text{sample solution dilution volume (mL)}} \times \frac{100 - H_2O\ (\%)}{100}$$

The results of HPLC analysis are shown below in Table 1 and in FIG. 1.

TABLE 1

Impurity Profile of PMPA Drug Substance by HPLC Method STM-1278-001
(% by Area Normalization)

| Lot. No. | RRT# | | | | | | | | | | | |
|---|---|---|---|---|---|---|---|---|---|---|---|---|
| | 0.38 | 0.64 Bis-adduct | 0.84 Adenine | 1.2 | 1.4 Hydroxy propyl adenine | 1.49 | 1.51 | 1.6 | 1.8 | 1.9 | 2.1 | Total Impurities |
| 964-187-31 Ref Std | nd | 0.15 | 0.08* | nd | 0.13 | nd | nd | 0.21 | nd | 0.10 | nd | 0.7 |
| 1016-56-26 | 0.08* | 0.89 | tr | nd | 0.27 | nd | nd | 0.71 | 0.08* | 0.23 | nd | 2.3 |
| 1039-96-11 | nd | nd | nd | nd | nd | nd | nd | nd | nd | nd | 0.10 (RRT 2.0) | 0.1 |
| 1278-A-1 | tr | 0.73 | tr | tr | 0.19 | tr | tr | 0.43 | tr | 0.20 | 0.06* | 1.6 |

Retention time relative to PMPA
*The levels reported are considered to be estimates of actual levels, since they are near or below the expected quantitation limit of the method.
tr: trace, estimated as <0.05%
nd: none detected, estimated as <0.02%

I claim:

1. A method comprising analyzing a PMPA composition to determine the presence or absence of at least one contaminant having an HPLC retention time relative to PMPA of 0.38, 0.64, 1.2, 1.4, 1.49, 1.51, 1.6, 1.8 or 1.9.

2. A method comprising analyzing a PMPA composition to determine the presence or absence of at least one contaminant found in trace 1 of FIG. 1 which is not found in trace 2 of FIG. 1.

3. A method comprising analyzing a PMPA composition to determine the presence or absence of at least one contaminant selected from the group of bisPMPA adduct, hydroxypropyl adenine and propenyl adenine.

* * * * *